United States Patent
Mitsui et al.

(10) Patent No.: US 6,281,389 B1
(45) Date of Patent: *Aug. 28, 2001

(54) METHOD FOR PURIFYING TETRAKIS (FLUOROARYL)BORATE COMPOUNDS OR TRIS(FLUOROARYL)BORATE COMPOUNDS

(75) Inventors: Hitoshi Mitsui, Kitakatsuragi-gun; Toshiya Iida, Suita; Ikuyo Ikeno, Osaka; Naoko Hirano, Nishinomiya; Yukiko Ariyoshi, Yamatokoriyama, all of (JP)

(73) Assignee: Nippon Shokubai Co., Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/391,585

(22) Filed: Sep. 7, 1999

(30) Foreign Application Priority Data

Sep. 7, 1998 (JP) .................................................. 10-252981

(51) Int. Cl.[7] .................................................. C07F 5/02
(52) U.S. Cl. .................................................. 568/1; 568/6
(58) Field of Search .................................................. 568/1, 6

(56) References Cited

U.S. PATENT DOCUMENTS

| | | | |
|---|---|---|---|
| 5,189,222 | 2/1993 | Ashby et al. | 568/1 |
| 5,340,898 | 8/1994 | Cavezzan et al. | 528/19 |
| 5,420,355 | 5/1995 | Ikeda et al. | 568/6 |
| 5,473,036 | 12/1995 | Piotrowski et al. | 528/4 |
| 5,488,169 | 1/1996 | Ikeda et al. | 568/3 |
| 5,600,005 | * 2/1997 | Naganuma et al. | 568/6 |
| 5,693,867 | * 12/1997 | Baur et al. | 568/1 |

FOREIGN PATENT DOCUMENTS

| | | |
|---|---|---|
| 0608563 A2 | 3/1994 | (EP) . |
| 0913400 A1 | 6/1999 | (EP) . |
| 6-247981 | 9/1994 | (JP) . |
| WO 96/27435 | 12/1996 | (WO) . |

OTHER PUBLICATIONS

"Perfluorophenyl Derivatives of the Elements I.Tris (Pentafluorophenyl) Boron", A.G. Massey, et al. *Journal of Organometallic Chemistry*, J. Organometal. Chem., 2(1964), pp. 245–250.

* cited by examiner

*Primary Examiner*—Jean F. Vollano
(74) *Attorney, Agent, or Firm*—David G. Conlin; Lisa Swiszcz Hazzard; Dike, Bronstein, Roberts & Cushman, IP Group

(57) ABSTRACT

A solution containing an organic solvent and a compound including impurities, represented by, for example, general formula (1)

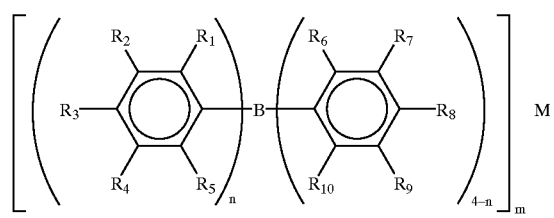

(1)

(wherein $R_1$ to $R_{10}$ independently represent H, F, a hydrocarbon group or an alkoxy group, at least one of $R_1$ to $R_5$ is F, at least one of $R_6$ to $R_{10}$ is F, M is H, alkali metal, alkaline earth metal or alkaline earth metal halide, n is 3 or 4, and m is 2 when M is an alkaline earth metal, or m is 1 when M is the other) is mixed with water. The purified compound is reacted with a compound which forms a monovalent cation seed to prepare a derivative. Thus, a purifying method capable of efficiently and easily separating and removing colored components contained in tetrakis(fluoroaryl)borate compounds can be provided. Moreover, it is possible to provide a method capable of preparing a highly-pure tetrakis (fluoroaryl)borate derivative efficiently and at low costs.

14 Claims, No Drawings

METHOD FOR PURIFYING TETRAKIS (FLUOROARYL)BORATE COMPOUNDS OR TRIS(FLUOROARYL)BORATE COMPOUNDS

FIELD OF THE INVENTION

The present invention relates to a method for purifying a tetrakis(fluoroaryl)borate compound or tris(fluroary)borate compound containing impurities. The present invention also relates to a method for preparing a tetrakis(fluoroaryl)borate derivative which is useful as, for example, a co-catalyst of a metallocene catalyst (polymerization catalyst) for a cationic complex polymerization reaction and a catalyst for photopolymerization of silicone.

BACKGROUND OF THE INVENTION

Tetrakis(fluoroaryl)borate derivatives are useful compounds as, for example, a co-catalyst for promoting the activity of a metallocene catalyst (polymerization catalyst) for a cationic complex polymerization reaction and a catalyst for photopolymerization of silicone. Moreover, tetrakis (fluoroaryl)borate compounds are compounds which are useful as intermediates for the preparation of the tetrakis (fluoroaryl)borate derivatives. In resent years, the metallocene catalyst is particularly noted as a catalyst for polymerization of polyolefin.

For instance, J. Organometal. Chem., 2 (1964), pp.245–250 discloses a method for synthesizing a tetrakis (pentafluorophenyl)borate derivative by reacting bromopenetafluorobenzene with butyl lithium (an organic lithium compound) at −78° C. with the use of dry pentane as a solvent to form pentafluorophenyl lithium, reacting this compound with a boron trichloride (halogenated boron) to synthesize a tris(pentaflourophenyl)borane, and reacting this compound with pentafluorophenyl lithium to synthesize the tetrakis(pentafluorophenyl)borate derivative. Moreover, Tokukaihei No. 6-247981 (Japanese laid-open patent application, published Sep. 6, 1994) discloses a method for synthesizing a tetrakis(pentafluorophenyl)borate-lithium that is a kind of tetrakis(fluoroaryl)borate compound from pentafluorobenzene with the use of an organic lithium compound and halogenated boron.

However, these methods suffer from the problems: 1) since the organic lithium compound is unstable with respect to heat, the temperature of the reaction system must be maintained at a temperature of not higher than −65° C., and therefore special facilities are required and it takes a cost for cooling; 2) since an expensive organic lithium compound must be used and ignition may occur by the reaction between the compound and water, etc, it is dangerous to handle the compound; and 3) since expensive halogenated boron must be used and the compound is in gaseous phase and corrosive, the compound is difficult to handle. It is thus difficult to industrially implement the method disclosed in the above-mentioned publications.

In contrast, for example, U.S. Pat. No. 5,473,036 discloses a method for preparing triethylammonium*tetrakis (pentafluorophenyl)borate by reacting bromopentafluorobenzene with magnesium to give pentafluorophenyl magnesium bromide, reacting this compound as a Grignard reagent with a boron trifluoride diethyl ether complex to synthesize tetrakis (pentafluorophenyl) borate magnesium bromide, and reacting this compound with triethylammonium-chloride to prepare the triethylammonium tetrakis(pentafluorophenyl) borate. Further, Tokukaihei No. 6-247980 (Japanese laid-open patent application, published Sep. 6, 1994) discloses a method for synthesizing a tetrakis(fluoroaryl)borate compound by a Grignard reaction, and more specifically a) a method for preparing a tetrakis(pentafluorophenyl)borate-magnesium halide by reacting a pentafluorophenyl magnesium halide with halogenated boron; and b) a method for preparing a tetrakis (pentafluorophenyl)borate magnesium halide by reacting a pentafluorophenyl magnesium halide with tris (pentafluorophenyl) boron.

In the preparation method of United States Patent No. 5,473,036, magnesium bromide fluoride and magnesium chloride fluoride are given as by-products together with triethylammonium tetrakis(pentafluorophenyl)borate. However, this publication does not disclose or mention separation and removal of the halogenated magnesium as the by-product from the reaction system. Since triethylammonium tetrakis(pentafluorophenyl)borate is a crude product, in order to obtain a final purified product, it is necessary to recrystallize the compound with the use of chloroform or methylene chloride/butyl ether. It is thus hard to say that the above preparation method is an industrially effective method.

Besides, in the above-mentioned preparation method a) of Tokukaihei No. 6–247980, halogenated magnesium is given as a by-product together with the tetrakis (pentafluorophenyl)borate. magnesium halide. However, this publication does not disclose or mention separation and removal of the halogenated magnesium as the by-products from the reaction system. When a tetrakis (pentafluorophenyl)borate derivative which is prepared with the use of tetrakis(pentafluorophenyl)borate-magnesium bromide containing halogenated magnesium as impurities is used as, for example, a co-catalyst of a metallocene catalyst, the activity of the catalyst is considerably owered. Therefore, the tetrakis(pentafluorophenyl)borate magnesium bromide prepared by this method is not suitable as the intermediate for the preparation of the tetrakis (pentafluorophenyl)borate derivative.

The pentafluorophenyl magnesium halide as a Grignard reagent used in the above U.S. Pat. No. 5,473,036 and Tokukaihei No. 6-247980 and more specifically, for example, pentafluorophenyl magnesium bromide formed from bromopentafluorobenzene and magnesium, is colored black by colored components as impurities produced by a side reaction, etc. Therefore, a tetrakis(fluoroaryl)borate compound synthesized with the use of the pentafluorophenyl magnesium halide is colored black by the colored components unless the step of removing the colored components is executed. Thus, when a tetrakis(fluoroaryl)borate derivative as an object is prepared using the tetrakis(fluoroaryl)borate compound, the tetrakis(fluoroaryl)borate derivative has a bad color tone. Hence, it is difficult to provide tetrakis (fluoroaryl)borate derivatives as products.

In short, the tetrakis(fluoroaryl)borate compound containing the colored components as impurities is not suitable as the intermediate for the preparation of a tetrakis(fluoroaryl) borate derivative. However, the above-mentioned publications do not disclose or mention the removal of the colored components.

Therefore, there is a great demand for a purifying method capable of efficiently and easily separating and removing colored components contained as impurities in tetrakis (fluoroaryl)borate compounds. There is also a great demand for a method capable of preparing a highly-pure tetrakis (fluoroaryl)borate derivative efficiently and at low costs.

SUMMARY OF THE INVENTION

It is an object of the present invention to provide a purifying method capable of efficiently and easily separating and removing colored components contained as impurities in tetrakis(fluoroaryl)borate compounds or tris(fluoroaryl) borate compounds.

It is another object of the present invention to provide a method capable of preparing a highly-pure tetrakis (fluoroaryl)borate derivative, which is useful as, for example, a co-catalyst of a metallocene catalyst and a catalyst for photopolymerization of silicone, efficiently and at low costs.

The inventors of the present invention eagerly studied on the method for purifying tetrakis(fluoroaryl)borate compounds, and the method for preparing tetrakis (fluoroaryl)borate derivatives. It was found as a result of the study that, by mixing a solution containing an organic solvent and a tetrakis (fluoroaryl) borate compound or tris(fluoroaryl)borate compounds including colored components as impurities, with water, the colored components can be efficiently and easily separated and removed. Further, the inventors found that a highly-pure tetrakis(fluoroaryl)borate derivative can be prepared efficiently and at low costs by reacting the tetrakis(fluoroaryl)borate compound or tris (fluoroaryl)borate compounds obtained by the above-mentioned purifying method with a compound generating a monovalent cation seed, and completed the present invention.

In order to achieve the above object, a method for purifying a tetrakis(fluoroaryl)borate compound or tris (fluoroaryl)borate compounds according to the present invention is a method characterized by mixing a solution containing an organic solvent and the tetrakis(fluoroaryl) borate compound or tris(fluoroaryl)borate compounds including impurities, with water.

Moreover, the method for purifying a tetrakis(fluoroaryl) borate compound or tris(fluoroaryl)borate compounds according to the present invention is characterized in that the tetrakis(fluoroaryl)borate compound or tris(fluoroaryl) borate compounds is a compound represented by general formula (1)

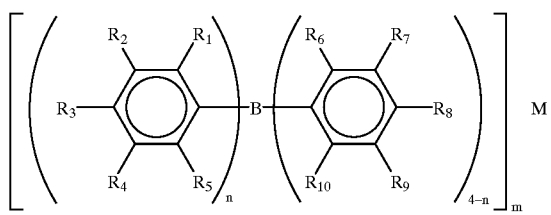

(1)

(wherein $R_1$, $R_2$, $R_3$, $R_4$, $R_5$, $R_6$, $R_7$, $R_8$, $R_9$ and $R_{10}$ independently represent a hydrogen atom, a fluorine atom, a hydrocarbon group or an alkoxy group, at least one of $R_1$ $R_5$ is a fluorine atom, at least one of $R_6$ to $R_{10}$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal).

Furthermore, the method for purifying a tetrakis (fluoroaryl)borate compound or tris(fluoroaryl)borate compounds according to the present invention is characterized by removing the organic solvent from the mixture by distillation after mixing the solution with water, or by further mixing an aqueous solution obtained by removing the organic solvent from the mixture by distillation after mixing the solution with water, with an aromatic hydrocarbon.

Additionally, the method for purifying a tetrakis(fluoroaryl) borate compound or tris(fluoroaryl)borate compounds according to the present invention is characterized by isolating the tetrakis(fluoroaryl)borate compound or tris (fluoroaryl)borate compounds as a solid from an aqueous solution of the tetrakis(fluoroaryl)borate compound or tris (fluoroaryl)borate compounds obtained by mixing the solution with water.

By adopting the above purifying method, since colored components contained as impurities in the tetrakis (fluoroaryl)borate compound or tris(fluoroaryl)borate compounds can be separated and removed efficiently and easily, it is possible to purify the tetrakis(fluoroaryl)borate compoundor tris(fluoroaryl)borate compounds. In addition, after the solution is mixed with water, by removing the organic solvent from the mixture by distillation, or by further mixing the aqueous solution obtained by removing the organic solvent from the mixture by distillation with an aromatic hydrocarbon, the colored components can be separated and removed more efficiently and easily.

Besides, by adopting the above purifying method, it is possible to is ot islate the tetrakis(fluoroaryl)borate compound as a solid (crystal).

In order to achieve the another object, a method for preparing a tetrakis(fluoroaryl)borate derivative according to the present invention is characterized by reacting a tetrakis(fluoroaryl)borate compound or tris(fluoroaryl) borate compounds obtained by the above purifying method with a compound which forms a monovalent cation seed.

Moreover, the method for preparing a tetrakis(fluoroaryl) borate derivative according to the present invention is characterized in that the tetrakis(fluoroaryl)borate derivative is a compound represented by general formula (2)

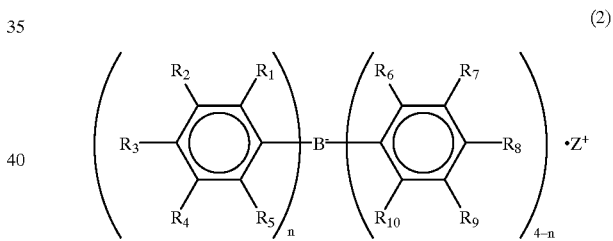

(2)

(wherein $R_1$, $R_2$, $R_3$, $R_4$, $R_5$, $R_6$, $R_7$, $R_8$, $R_9$ and $R_{10}$ independently represent a hydrogen atom, a fluorine atom, a hydrocarbon group or an alkoxy group, at least one of $R_1$ to $R_5$ is a fluorine atom, at least one of $R_6$ to $R_{10}$ is a fluorine atom, $Z^+$ is a monovalent cation seed, and n is 3 or 4).

By adopting the above preparation method, it is possible to prepare efficiently a tetrakis(fluoroaryl)borate derivative from a tetrakis(fluoroaryl)borate compound obtained by the above purifying method, at low costs. Since the derivative does not contain colored components as impurities, it has a satisfactory color tone and high purity. It is thus possible to use the derivative suitably as, for example, a co-catalyst of a metallocene catalyst for a cationic complex polymerization reaction and a catalyst for photopolymerization of silicone.

Further objects, the nature and advantages of the present invention will be understood by the following description. Also, the effects of the present invention will be explained clearly in the following description.

DESCRIPTION OF THE PREFERRED EMBODIMENT

A method for purifying a tetrakis(fluoroaryl)borate compound or tris(fluoroaryl)borate compounds of the present invention is a process of mixing a solution containing an organic solvent and the tetrakis(fluoroaryl)borate compound or tris(fluoroaryl)borate compounds including impurities, with water. The water may be distilled water, ion-exchange water, or pure water. The tetrakis(fluoroaryl)borate compound or tris(fluoroaryl)borate compounds is suitable as an intermediate of a tetrakis(fluoroaryl)borate derivative. Moreover, a method for preparing a tetrakis(fluoroaryl) borate derivative of the present invention is a process of reacting the tetrakis(fluoroaryl)borate compound or tris (fluoroaryl)borate compounds obtained by the above-mentioned purifying method with a compound which forms a monovalent cation seed.

The tetrakis(fluoroaryl)borate compound or tris (fluoroaryl)borate compounds to be purified by the present invention is not particularly restricted if it is a borate compound having at least three fluoroaryl groups which are formed by substitution of at least one of hydrogen atoms of an aryl group with a fluorine atom. More specifically, the tetrakis(fluoroaryl)borate compound or tris(fluoroaryl) borate compounds to be purified by the present invention is a compound represented by general formula (3)

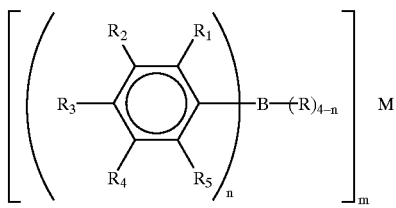

(3)

(wherein R is an alkyl group having 1 to 20 carbon atoms or a cycloalkyl group having 3 to 10 carbon atoms, $R_1$, $R_2$, $R_3$, R and $R_5$ independently represent a hydrogen atom, a fluorine atom, a hydrocarbon group or an alkoxy group, at least one of $R_1$ to $R_5$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal) . More specifically, the alkyl group of the substituent group represented by R in the formula is a straight-chain or branched-chain alkyl group.

Among the compounds, a tetrakis(fluoroaryl)borate compound represented by general formula (1) above is more suitable. The following description will explain the present invention by illustrating the tetrakis(fluoroaryl)borate compound represented by general formula (1) above as an example.

The tetrakis(fluoroaryl)borate compound of general formula (1) to be purified by the present invention is a compound, wherein substituent groups represented by $R_1$ to $R_{10}$ in the formula are independently formed by a hydrogen atom, fluorine atom, hydrocarbon group or alkoxy group, at least one of the substituent groups represented by $R_1$ to $R_5$ is a fluorine atom, at least one of the substituent groups represented by $R_6$ to $R_{10}$ is a fluorine atom, a substituent group represented by M is formed by a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal.

Therefore, the tetrakis(fluoroaryl)borate compounds are specifically alkali metal salts of tetrakis(fluoroaryl)borates, alkaline earth metal salts of tetrakis(fluoroaryl)borates, alkaline earth metal halide salts of tetrakis(fluoroaryl)borates, and hydrogen compounds of tetrakis(fluoroaryl)borates.

Specifically, the hydrocarbon group is an aryl group, a straight-chain, branched-chain or cyclic alkyl group having 1 to 12 carbon atoms, a straight-chain, branched-chain or cyclic alkenyl group having 2 to 12 carbon atoms, etc. The hydrocarbon group may further include a functional group inert to the purification (process) and reaction of the present invention. Specific examples of the functional group include a methoxy group, methylthio group, N,N-dimethylamino group, o-anise group, p-anise group, trimethylsilyloxy group, dimethyl-t-butylsilyloxy group, and trifluoromethyl group.

The alkoxy group is represented by general formula (A)

(A)

(wherein $R_a$ is a hydrocarbon group), and the hydrocarbon group represented by $R_a$ in the formula is specifically, for example, an aryl group, a straight-chain, branched-chain or cyclic alkyl group having 1 to 12 carbon atoms, or a straight-chain, branched-chain or cyclic alkenyl group having 2 to 12 carbon atoms. The hydrocarbon group may further include a functional group inert to the purification (process) and reaction of the present invention.

Specific examples of the alkoxy group represented by the general formula (A) include a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, and a phenoxy group.

Prior to describe in great detail the purifying method of the present invention, an example of the method for preparing the tetrakis(fluoroaryl)borate compounds will be explained below.

The tetrakis(fluoroaryl)borate compounds can be prepared by ① a process of treating tetrakis(fluoroaryl)borate-magnesium halide represented by general formula (4)

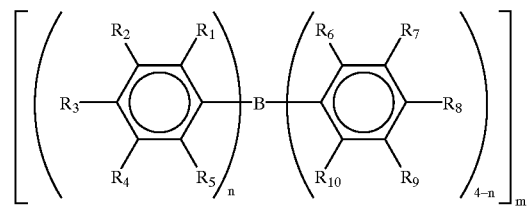

(4)

(wherein $R_1$, $R_2$, $R_3$, $R_4$, $R_5$, $R_6$, $R_7$, $R_8$, $R_9$ and $R_{10}$ independently represent a hydrogen atom, a fluorine atom, a hydrocarbon group or an alkoxy group, at least one of $R_1$ to $R_5$ is a fluorine atom, at least one of $R_6$ to $R_{10}$ is a fluorine atom, X is a chlorine atom, bromine atom or iodine atom, and n is 3 or 4) with a carboxylic acid alkali metal salt and/or carboxylic acid alkaline earth metal salt; ② a process of treating the tetrakis(fluoroaryl)borate·magnesium halide with an acid; ③ a process of treating the tetrakis(fluoroaryl) borate magnesium halide with an alkali metal hydroxide and/or alkaline earth metal hydroxide after treating it with an acid; and ④ a process of treating the tetrakis(fluoroaryl) borate·magnesium halide with a carboxylic acid alkali metal salt and/or carboxylic acid alkaline earth metal salt after treating it with an acid.

Therefore, when the tetrakis(fluoroaryl) borate magnesium halide is treated with a carboxylic acid alkali metal salt and/or carboxylic acid alkaline earth metal salt, or when it is treated with an alkali metal hydroxide and/or alkaline earth metal hydroxide, i.e., when the tetrakis(fluoroaryl)

borate·magnesium halide is treated by any of the above processes ①, ① and ①, an alkali metal salt of tetrakis (fluoroaryl)borate and/or an alkaline earth metal salt of tetrakis(fluoroaryl)borate and/or an alkaline earth metal halide salt of tetrakis(fluoroaryl)borate are obtained. Meanwhile, when the tetrakis(fluoroaryl)borate·magnesium halide is treated with an acid, i.e., when it is treated by the above process ②, a hydrogen compound of tetrakis (fluoroaryl)borate is obtained.

Besides, the tetrakis(fluoroaryl)borate·magnesium halide can be easily obtained by, for example, a process of reacting a halogenated aryl fluoride with magnesium to form fluoroaryl magnesium halide as a Grignard reagent and then reacting the fluoroaryl magnesium halide with halogenated boron in a mole ratio of 4:1. Hence, the tetrakis(fluoroaryl) borate·magnesium halide is obtained in the state of a reaction solution dissolved in a solvent used for a Grignard reaction.

The solvent is not particularly limited, and specific examples of the solvent include solvents of the ether series, such as diethyl ether, dipropyl ether, diisopropyl ether, dibutyl ether, t-butyl methyl ether, diisoamyl ether, 1,2-dimethoxyethane, 1,2-diethoxyethane, anisole, tetrahydrofuran, tetrahydropyran, and 1,4-dioxane; solvents of the aliphatic hydrocarbon series, such as pentane, hexane, and heptane; solvents of the alicyclic hydrocarbon series, such as cyclopentane, cyclohexane, and methylcyclohexane; and solvents of the aromatic hydrocarbon series, such as benzene, toluene, and xylene. These solvents may be used as a combined solvent.

Incidentally, the above-mentioned reaction solution contains colored components as impurities formed by a side reaction, etc. Besides, when the tetrakis(fluoroaryl) borate·magnesium halide is produced by reacting a fluoroaryl magnesium halide with halogenated boron, the halogenated magnesium as the by-product, for example, magnesium bromide fluoride is dissolved as an impurity in the solution.

Specific examples of carboxylic acid alkali metal salts used for the above treatment processes include:

alkali metal salts of saturated aliphatic monocarboxylic acids, such as sodium formate, potassium formate, sodium acetate, potassium acetate, sodium propionate, and potassium propionate;

monoalkali or dialkali metal salts of saturated aliphatic dicarboxylic acids, such as monosodium oxalate, disodium oxalate, monopotassium oxalate, dipotassium oxalate, monosodium malonate, disodium malonate, monopotassium malonate, dipotassium malonate, monosodium succinate, disodium succinate, monopotassium succinate, and dipotassium succinate;

alkali metal salts of unsaturated aliphatic monocarboxylic acids, such as solidum acrylate, potassium acrylate, sodium methacrylate, and potassium methacrylate;

monoalkali or dialkali metal salts of unsaturated aliphatic dicarboxylic acids, such as monosodium maleate, disodium maleate, monopotassium maleate, dipotassium maleate, monosodium fumarate, disodium fumarate, monopotassium fumarate, and dipotassium fumarate;

alkali metal salts of aromatic monocaroboxilic acids, such as sodium benzoate, and potassium benzoate; and monoalkali or dialkali metal salts of aromatic dicarboxilic acids, such as monosodium phthalate, disodium phthalate, monopotassium phthalate, dipotassium phthalate, monosodium isophthalate, disodium isophthalate, monopotassium isophthalate, dipotassium isophthalate, monosodium terephthalate, disodium terephthalate, monopotassium terephthalate, and dipotassium terephthalate. However, the carboxylic acid alkali metal salts are not particularly limited to these examples. Note that, in the present invention, the carboxylic acid alkali metal salts include carbonates such as lithium carbonate, sodium carbonate, sodium bicarbonate, potassium carbonate, and potassium bicarbonate.

Specific examples of carboxylic acid alkaline earth metal salts include:

alkaline earth metal salts of saturated aliphatic monocarboxylic acids, such as calcium formate, barium formate, calcium acetate, barium acetate, calcium propionate, and barium propionate;

alkaline earth metal salts of saturated aliphatic dicarboxylic acids, such as calcium oxalate, barium oxalate, calcium malonate, barium malonate, calcium succinate, and barium succinate;

alkaline earth metal salts of unsaturated aliphatic monocarboxylic acids, such as calcium acrylate, barium acrylate, calcium methacrylate, and barium methacrylate;

alkaline earth metal salts of unsaturated aliphatic dicarboxylic acids, such as calcium maleate, barium maleate, calcium fumarate, and barium fumarate;

alkaline earth metal salts of aromatic monocaroboxilic acids, such as calcium benzoate, and barium benzoate; and alkaline earth metal salts of aromatic dicarboxilic acids, such as calcium phthalate, barium phthalate, calcium isophthalate, barium isophthalate, calcium terephthalate, and barium terephthalate. However, the carboxylic acid alkaline earth metal salts are not particularly limited to these examples. Note that, in the present invention, the carboxylic acid alkaline earth metal salts include carbonates, such as calcium carbonate and barium carbonate. However, in the present invention, the carboxylic acid alkaline earth metal salts do not include carboxylic acid magnesium salts.

Only one kind or more than one kind of these carboxylic acid alkali metal salts and carboxylic acid alkaline earth metal salts (the general term "carboxylate" is hereinafter used to refer to both of these salts). Among the exemplified carboxylates, lithium carbonate, solidum carbonate, potassium carbonate, sodium acetate, disodium succinate, and barium acetate are particularly preferred. The amount of carboxylate used is not particularly restricted if it is not less than one equivalent of tetrakis(fluoroaryl)borate·magnesium halide. Moreover, when the carboxylic acid alkali metal salt and carboxylic acid alkaline earth metal salt are used together, the ratio thereof is not particularly restricted.

Specific examples of the acid used for the above-mentioned treatment processes include: inorganic acids, such as hydrochloric acid, sulfuric acid, nitric acid, phosphoric acid, and carbonic acid; and organic acids, such as formic acid, acetic acid, propionic acid, oxalic acid, malonic acid, and succinic acid. However, the acid is not particularly limited to these examples.

It is possible to use only one kind or more than one kind of these acids. Among the exemplified acids, hydrochloric acid, sulfuric acid, formic acid, acetic acid, oxalic acid and malonic acid are particularly preferred. The amount of acid used is not particularly restricted if it is not less than one equivalent of magnesium used for the preparation of tetrakis (fluoroaryl)borate·magnesium halide (introduced into the reaction system). Moreover, when an inorganic acid and an organic acid are used together, the ratio thereof is not particularly restricted.

Specific examples of the alkali metal hydroxide used for the above-mentioned treatment processes include lithium hydroxide, sodium hydroxide, and potassium hydroxide. Besides, specific examples of the alkaline earth metal hydroxide used for the above-mentioned treatment processes include calcium hydroxide and barium hydroxide. In the present invention, however, the alkaline earth metal hydroxides do not include magnesium hydroxide.

Only one or more than one kind of these alkali metal hydroxides and alkaline earth metal hydroxides (the general term "hydroxides" is hereinafter used to refer to both of these hydroxides). The amount of hydroxide used is not particularly restricted if it is not less than one equivalent of tetrakis(fluoroaryl)borate·magnesium halide. Moreover, when the alkali metal hydroxide and alkaline earth metal hydroxide are used together, the ratio thereof is not particularly restricted.

When treating the tetrakis(fluoroaryl) borate·magnesium halide with a carboxylate (the above-mentioned process ①), the tetrakis(fluoroaryl)borate·magnesium halide and carboxylate can be mixed and stirred. When treating the tetrakis (fluoroaryl) borate·magnesium halide with an acid (the above-mentioned process ②), the tetrakis(fluoroaryl) borate·magnesium halide and acid can be mixed and stirred. Further, when treating the tetrakis (fluoroaryl) borate·magnesium halide with a hydroxide after treating it with an acid (the above-mentioned process ①, the tetrakis (fluoroaryl)borate·magnesium halide and hydroxide can be mixed and stirred after separating and removing the acid. Meanwhile, when treating the tetrakis(fluoroaryl) borate·magnesium halide with a carboxylate after treating it with an acid (the above-mentioned process ①, the tetrakis (fluoroaryl)borate·magnesium halide and carboxylate can be mixed and stirred after separating and removing the acid.

The method of mixing a solution of tetrakis(fluoroaryl) borate·magnesium halide with the carboxylate, acid or hydroxide is not particularly limited. The carboxylate, acid and hydroxide can be mixed in the present state (solid or liquid), or in the state of solution if necessary, with the solution of tetrakis(fluoroaryl)borate·magnesium halide.

Specifically, when the carboxylate, acid and hydroxide are in the state of solution, suitable examples of solvent include: water; the above-exemplified solvents of the ether series; the above-exemplified solvents of the aliphatic hydrocarbon series; the above-exemplified solvents of the alicyclic hydrocarbon series; solvents of the ester series, such as methyl acetate and ethyl acetate; the above-exemplified solvents of the aromatic hydrocarbon series; solvents of the alcohol series, such as methyl alcohol and ethyl alcohol; and solvents of the ketone series, such as acetone and methyl ethyl ketone. However, the solvent is not particularly limited to these examples. It is possible to use only one kind or more than one kind of these solvents.

The method and order of mixing the carboxylate, acid or hydroxide are not particularly restricted. For instance, it is possible to mix the carboxylate, acid or hydroxide in the solution of tetrakis(fluoroaryl)borate·magnesium halide. Alternatively, it is possible to mix the solution of tetrakis (fluoroaryl)borate·magnesium halide in the carboxylate, acid or hydroxide.

The temperature and time, i.e., conditions, of mixing and stirring the solution of tetrakis (fluoroaryl)borate. magnesium halide with the carboxylate, acid or hydroxide are not particularly restricted. According to the above-described treatment processes, the tetrakis(fluoroaryl) borate·magnesium halide can be easily treated by mixing the solution of tetrakis (fluoroaryl)borate·magnesium halide with the carboxylate, acid or hydroxide and then stirring them at room temperature for a predetermined time. Moreover, when treating the tetrakis (fluoroaryl) borate·magnesium halide with a hydroxide or carboxylate after treating it with an acid, the method of separating and removing the acid is not particularly restricted. For example, the acid can be separated from the solution of tetrakis (fluoroaryl)borate compound by performing simple separation (oil and water separation). After the treatment, the tetrakis (fluoroaryl)borate compound is obtained in the state of solution, i.e., in the state in which it is dissolved in a solvent (organic solvent).

When the solution of tetrakis(fluoroaryl) borate.magnesium halide contains the carboxylate, acid or hydroxide, the carboxylate, acid or hydroxide can be removed by performing washing, etc., if necessary. On the other hand, when the carboxylate, acid, hydroxide or the solution thereof contains the tetrakis(fluoroaryl)borate compound, the tetrakis (fluoroaryl)borate compound can be recovered by performing extraction, etc., if necessary. Further, when water is contained in the solution of tetrakis(fluoroaryl)borate compound, water can be removed (dried) by adding a desiccant, such as anhydrous magnesium sulfate, if necessary.

By treating the tetrakis(fluoroaryl) borate.magnesium halide according to the above processes ① to ④, a tetrakis (fluoroaryl) borate compound to be purified by the present invention is obtained. In other words, when the tetrakis (fluoroaryl) borate.magnesium halide is treated with the carboxylate or hydroxide, i.e., treated with the above-described processes ①, ③ and ④, tetrakis(fluoroaryl) borates wherein M in general formula (1) above is an alkali metal, alkaline earth metal or alkaline earth metal halide are obtained. On the other hand, when the tetrakis(fluoroaryl) borate·magnesium halide is treated with an acid, i.e., treated with the above-described process ②, a hydrogen compound of a tetrakis(fluoroaryl)borate wherein M in general formula (1) above is a hydrogen atom is obtained.

Among the above-described treatment processes ① to ④, for example, a suitable process can be selected on the basis of the kind of tetrakis (fluoroaryl)borate·magnesium halide, the kind of solvent, etc. so that a tetrakis(fluoroaryl) borate compound in desired form (alkali metal salt, alkaline earth metal salt, alkaline earth metal halide salt or hydrogen compound) is obtained, or that the separation, for example, liquid separation, performed after the treatment is facilitated.

According to the above-mentioned treatment processes, it is possible to convert, for example, halogenated magnesium, which is given as a by-product during the preparation of the tetrakis(fluoroaryl)borate·magnesium halide by a Grignard reaction, into the state of a water-soluble magnesium salt or water-insoluble magnesium salt (i.e., the state of a salt other than magnesium hydroxide). Therefore, for example, by separating or filtering the salt contained in the tetrakis (fluoroaryl)borate·magnesium halide, it is possible to separate or remove the salt efficiently and easily from the solution of tetrakis(fluoroaryl)borate compound. In other words, impurities such as halogenated magnesium contained in the tetrakis(fluoroaryl)borate·magnesium halide can be efficiently and easily separated and removed.

The method of separating and removing impurities from the solution of tetrakis(fluoroaryl)borate compound is not particularly restricted. When a tetrakis(fluoroaryl)borate derivative is produced using a tetrakis(fluoroaryl)borate compound containing halogenated magnesium as impurities, the tetrakis(fluoroaryl)borate derivative also contains halogenated magnesium as impurities. When the tetrakis(fluoroaryl)borate derivative containing the halogenated magnesium is used as, for example, a co-catalyst of a metallocene catalyst, the activity of the catalyst is considerably lowered. Therefore, the tetrakis(fluoroaryl)borate compound containing the halogenated magnesium is not suitable as the intermediate for the preparation of the tetrakis(fluoroaryl)borate derivative.

Besides, for example, even when the tetrakis(fluoroaryl) borate·magnesium halide does not contain impurities such as halogenated magnesium, it is preferred to obtain a hydrogen compound of tetrakis(fluoroaryl)borate, an alkali metal salt of tetrakis(fluoroaryl)borate, an alkaline earth metal salt of tetrakis(fluoroaryl)borate, or an alkaline earth metal halide salt of tetrakis(fluoroaryl)borate by performing the above-described treatment. It is possible to promptly and efficiently proceed the reaction between such a salt and a compound which forms a monovalent cation seed.

Incidentally, the method for preparing a tetrakis(fluoroaryl)borate compound is not necessarily limited to those exemplified above. It is possible to prepare tetrakis(fluoroaryl)borate·magnesium halide as one kind of tetrakis(fluoroaryl)borate compound by, for example, a process of reacting fluoroaryl magnesium halide and tris(fluoroaryl) boron in a mole ratio of 1:1.

With the above-mentioned preparation method, a solution containing a tetrakis(fluoroaryl)borate compound which does not contain halogenated magnesium such as magnesium bromide fluoride, i.e., a crude tetrakis(fluoroaryl) borate compound, and an organic solvent (hereinafter simply referred to as the "solution") is obtained. However, this solution contains colored components as impurities. The concentration (content) of the tetrakis(fluoroaryl)borate compound in the solution is not particularly restricted. However, in order to implement the purifying method of the present invention, a higher concentration is preferred.

Next, the following description will explain the purifying method of the present invention.

According to the purifying method of the present invention, the above solution is mixed with water. The tetrakis(fluoroaryl)borate compound or tris(fluoroaryl) borate compound is soluble in water. On the other hand, the colored components which are given as by-product impurities during the preparation of the tetrakis(fluoroaryl)borate compound or tris(fluoroaryl)borate compound by the Grignard reaction are not soluble in water. Therefore, when the solution and water are brought into contact with each other by, for example, mixing and stirring, the tetrakis(fluoroaryl) borate compound or tris(fluoroaryl)borate compound moves toward the aqueous layer side, while the colored components remain on the solution side (organic solvent side), i.e., remain on the oily layer side. Hence, for example, by separating the mixture obtained by mixing and stirring the solution and water into two layers and then separating the aqueous layer and oily layer (oil and water separation), the tetrakis(fluoroaryl)borate compound or tris(fluoroaryl) borate compound and the colored components can be separated and removed efficiently and easily. In other words, it is possible to purify the tetrakis(fluoroaryl)borate compound or tris(fluoroaryl)borate compound because the colored components can be separated and removed.

The mixing ratio of the solution and water, i.e., the amount of water to the tetrakis(fluoroaryl)borate compound or tris(fluoroaryl)borate compound, can be set according to a mixing temperature (described later), the solubility of the tetrakis(fluoroaryl)borate compound or tris(fluoroaryl) borate compound at the temperature, etc., and is not particularly restricted. For instance, the amount of water can be set so that the ratio of the tetrakis(fluoroaryl)borate compound or tris(fluoroaryl)borate compound to the total amount of the tetrakis(fluoroaryl)borate compound or tris (fluoroaryl)borate compound and water is within the range of preferably from 0.1% by weight to 90% by weight, more preferably from 1% by weight to 50% by weight, and most preferably from 10% by weight to 50% by weight. When the amount of water exceeds the above-mentioned range, the amount of the aqueous layer is increased, and there is a possibility that the tetrakis(fluoroaryl)borate compound or tris(fluoroaryl)borate compound is not purified efficiently. On the other hand, when the amount of water is less than the above-mentioned range, since the tetrakis(fluoroaryl)borate compound or tris(fluoroaryl)borate compound to be moved to the aqueous layer side remains on the oily layer side, there is a possibility that the tetrakis(fluoroaryl)borate compound or tris(fluoroaryl)borate compound is not purified efficiently.

The method of mixing the solution and water and the mixing order are not particularly restricted. For instance, water may be mixed and stirred in the solution, or the solution may be mixed and stirred in water. At this time, water may be introduced into the solution by dropping, or the solution may be introduced into water by dropping. Alternatively, a method of continuously extracting the tetrakis(fluoroaryl)borate compound or tris(fluoroaryl) borate compound from the solution with the use of water as an extractive medium by an apparatus such as a Soxhlet extractor for heavy specific gravity can be employed as the above-mentioned mixing method. Accordingly, in the present invention, "mixing the solution with water" includes "separating the solution from water while continuously contacting the solution with water".

Moreover, the mixing temperature and time when mixing the solution with water, i.e., the purifying conditions, are not particularly restricted. According to the purifying method of the present invention, after mixing the solution with water, for example, they can be stirred for a predetermined time at a temperature which is higher than the freezing point of water but is not higher than the boiling point of water, i.e., within the range of from 0° C. to 100° C., and more preferably from 50° C. to 100° C. within which the tetrakis (fluoroaryl)borate compound has a higher solubility and is dissolved more efficiently. Besides, the solution and water may be adjusted to a predetermined temperature (i.e., the mixing temperature) prior to mixing. Alternatively, the mixture obtained by the mixing may be adjusted to the predetermined temperature. In short, according to the purifying method of the present invention, the aqueous layer and the oily layer need to reach the mixing temperature at the time of separation of the aqueous layer and oily layer (oil and water separation). Incidentally, the method of adjusting the solution and water, or the mixture, to the predetermined temperature is not particularly restricted.

Moreover, in the purifying method of the present invention, after mixing the solution and water, by removing the organic solvent from the mixture by distillation or further mixing an aqueous solution obtained by the removal of the organic solvent from the mixture by distillation with an aromatic hydrocarbon with, if necessary, it is possible to more efficiently purify the tetrakis(fluoroaryl)borate compound or tris(fluoroaryl)borate compound. In other words, by removing the organic solvent by distillation, or more specifically by removing the organic solvent by distillation, so that the weight of the organic solvent to the weight of the water is equal to or less than 30% by weight, an increased amount of the tetrakis(fluoroaryl)borate compound or tris (fluoroaryl)borate compound which is dissolved in the oily layer (organic solvent) can dissolve in water. It is thus possible to purify the tetrakis(fluoroaryl)borate compound or tris(fluoroaryl)borate compound more efficiently.

The method or the conditions such as temperature, pressure and time, for removing the organic solvent by distillation are not particularly restricted. When the organic solvent forms an azeotropic composition with water, the temperature is preferably set to the azeotropic temperature. When the organic solvent does not form an azeotropic composition with water, the temperature is preferably set to a temperature equal to or higher than the boiling point of the organic solvent. Moreover, when the organic solvent forms the azeotropic composition with water, the water removed together with the organic solvent by distillation may be returned to the mixture after the separation, or discarded. Alternatively, new water equivalent to the amount of the water removed by distillation may be added to the mixture. The pressure can be either normal pressure (atmospheric pressure) or reduced pressure. Hence, when removing the organic solvent by distillation, the organic solvent is preferably a compound which forms an azeotropic composition with water or a compound whose boiling point at normal pressure is lower than 100° C. Further, after mixing the solution with water, the organic solvent may be removed from the mixture by distillation. Alternatively, the organic solvent may be removed by distillation while introducing the solution into water by dropping. Incidentally, the heating method in removing the organic solvent by distillation is not particularly restricted.

When the aqueous layer and the oily layer are present after removing the organic solvent by distillation, usually, the oily layer is present as the upper layer and the aqueous layer is present as the lower layer. The method or the conditions such as the temperature and time, for separating the aqueous layer and the oily layer (oil and water separation) is not particularly restricted. However, in order to prevent separation of the tetrakis(fluoroaryl)borate compound or tris(fluoroaryl)borate compound dissolved in the aqueous layer or to limit the lowering of the flowability of the aqueous layer, the temperature needs to be set to a temperature which is higher than the freezing point of the aqueous layer but is lower than the boiling point of the aqueous layer, and more preferably to a temperature around 50° C. Incidentally, when the organic solvent forms an azeotropic composition with water, the temperature needs to be set to a temperature which is higher than the freezing point of the aqueous layer but is lower than the azeotropic temperature.

By the way, when the organic solvent is almost completely removed by distillation, the colored components become, for example, oily droplets, and sink because the specific gravity of the droplets is greater than that of the aqueous layer (aqueous solution) . In this case, by extracting the aqueous layer or the droplets, it is possible to separate the tetrakis(fluoroaryl)borate compound or tris(fluoroaryl) borate compound from the colored components. Alternatively, in order to facilitate the separation of the colored components, it is possible to dissolve the colored components in an aromatic hydrocarbon by mixing the aromatic hydrocarbon with the aqueous layer and then separate the aqueous layer and the aromatic hydrocarbon layer.

As the aromatic hydrocarbon, it is possible to use a compound which dissolves the colored components but does not dissolve the tetrakis(fluoroaryl)borate compound or tris (fluoroaryl)borate compound. Specific examples of the aromatic hydrocarbon may include benzene, toluene, xylene, mesitylene, durene, ethylbenzene, and cumene. However, the aromatic hydrocarbon is not particularly limited to these examples. It is possible to use only one kind or a mixture of more than one kinds of these compounds.

The amount of aromatic hydrocarbon used is not particularly restricted if it can dissolve the colored components sufficiently. For instance, the amount of aromatic hydrocarbon can be set so that the weight ratio of the tetrakis (fluoroaryl)borate compound or tris(fluoroaryl)borate compound to the aromatic hydrocarbon is preferably within the range between 1:0.01 and 1:10, and more preferably between 1:0.1 and 1:5. When the amount of aromatic hydrocarbon used exceeds the above range, the amount of aromatic hydrocarbon layer is increased, and thus there is a possibility that the tetrakis(fluoroaryl)borate compound or tris(fluoroaryl)borate compound is not efficiently purified.

The method of mixing the aqueous layer and the aromatic hydrocarbon and the mixing order are not particularly restricted. For instance, the aromatic hydrocarbon may be mixed and stirred in the aqueous layer, or the aqueous layer may be mixed and stirred in the aromatic hydrocarbon. Alternatively, a method of continuously extracting the colored components from the aqueous layer with the use of the aromatic hydrocarbon as an extraction medium by an apparatus such as a Soxhlet extractor for heavy specific gravity can be employed as the above-mentioned mixing method. Accordingly, in the present invention, "mixing the aqueous layer with the aromatic hydrocarbon" includes "separating the aqueous layer and the aromatic hydrocarbon while continuously contacting the aqueous layer with the aromatic hydrocarbon".

Moreover, the conditions such as the mixing temperature and time when mixing the aqueous layer with the aromatic hydrocarbon are not particularly restricted, and for example, can be set according to the above-mentioned conditions for mixing the solution with water. After separating a mixture obtained by mixing and stirring the aqueous layer and the aromatic hydrocarbon into two layers, by separating the aqueous layer from the aromatic hydrocarbon layer (oil and water separation), it is possible to efficiently and easily separate and remove the tetrakis(fluoroaryl)borate compound and the colored components.

When the aqueous layer and the oily layer are separated without removing the organic solvent by distillation or when the aqueous layer and the oily layer are separated in a state in which the organic solvent is removed to certain extent by distillation, in order to further remove impurities contained in the aqueous layer, it is possible to mix the aqueous layer and aromatic hydrocarbon to dissolve (extract) the impurities in the aromatic hydrocarbon and then separate the aqueous layer and the aromatic hydrocarbon layer. With this process, it is possible to purify the tetrakis(fluoroaryl)borate compound or tris(fluoroaryl)borate compound to have higher purity.

With the above-described purifying method, the tetrakis (fluoroaryl)borate compound containing no colored components as impurities, i.e., an aqueous solution of the tetrakis (fluoroaryl)borate compound or tris(fluoroaryl)borate compound is obtained.

Besides, when isolating and purifying the tetrakis (fluoroaryl)borate compound or tris(fluoroaryl)borate compound as a solid (crystal) from the aqueous solution of the tetrakis(fluoroaryl)borate compoundor tris(fluoroaryl)borate compound, various processes can be further performed, for example, water is completely removed from the aqueous solution by distillation; the aqueous solution can be condensed and/or cooled to separate the compound, and then the separation process such as filtration is performed; or the compound is extracted from the aqueous solution by mixing the aqueous solution with an organic extraction medium, and then the organic extraction medium is removed by distillation. In particular, when water-soluble impurities are contained in the aqueous solution of the tetrakis(fluoroaryl)borate compoundor tris(fluoroaryl)borate compound, it is preferred to perform the process using the organic extraction medium.

The method of removing water completely from the aqueous solution by distillation and the various conditions such as temperature, pressure and time of the method are not particularly restricted. A specific example of such a method is a method of condensing and drying the aqueous solution under normal pressure or reduced pressure. The method of separating the compound by condensing and/or cooling the aqueous solution and the method of separating the compound by filtration, and various conditions such as the temperature, pressure and time of these methods are not particularly restricted.

As the above-mentioned organic extraction medium, it is possible to use a compound which dissolves the tetrakis(fluoroaryl)borate compound or tris(fluoroaryl)borate compound and is not evenly mixed with water. Examples of the organic extraction medium include: extraction media of the ether series, such as diethyl ether, dipropyl ether, diisopropyl ether, dibutyl ether, t-butyl methyl ether, diisoamyl ether, 1,2-dimethoxyethane, 1,2-diethoxyethane, anisole, 2-methyltetrahydrofuran, and 1,2-dioxane; extraction media of the ester series, such as methyl acetate, and ethyl acetate; extraction media of the ketone series, such as diethyl ketone and dipropyl ketone; and extraction media of the chlorine series, such as methylene chloride (dichloromethane), chloroform, and 1,2-dichloroethane. However, the organic extraction medium is not necessarily limited to these examples. It is possible to use only one kind or more than one kind of these organic extraction media.

The amount of the organic extraction medium used is not particularly restricted if the tetrakis(fluoroaryl)borate compound or tris(fluoroaryl)borate compound is sufficiently extracted from the aqueous solution. When an extraction using the organic extraction medium is performed, the tetrakis(fluoroaryl)borate compound or tris(fluoroaryl)borate compound moves to the oily layer side (organic extraction medium side), while various water-soluble impurities remain on the aqueous layer side (aqueous solution side). Therefore, for example, by separating the mixture obtained by mixing and stirring the aqueous solution with the organic extraction medium into two layers and then separating the aqueous layer from the oily layer (water and oil separation), the tetrakis(fluoroaryl)borate compound or tris(fluoroaryl)borate compound and the water-soluble impurities can be efficiently and easily separated and removed.

The extraction method by mixing the aqueous solution with the organic extraction medium and the mixing order are not particularly restricted. For instance, the extraction may be performed by mixing and stirring the organic extraction medium in the aqueous solution, or by mixing and stirring the aqueous solution in the organic extraction medium. At this time, the organic extraction medium may be introduced into the aqueous solution by dropping, or the aqueous solution may be introduced into the organic extraction medium by dropping. Moreover, in the present invention "extraction of the compound by mixing the aqueous solution with the organic extraction medium" includes "separation of the compound while extracting the compound by continuous contact of the aqueous solution with the organic extraction medium". The method in which the organic extraction medium is removed by distillation after extracting the compound from the aqueous solution and various conditions such as temperature, pressure and time of the method are not particularly restricted. Hence, the method of extracting the tetrakis(fluoroaryl)borate compound or tris(fluoroaryl)borate compound from the aqueous solution using the organic extraction medium and the extraction conditions are not particularly restricted.

According to the above-mentioned purifying method, it is possible to islate the tetrakis(fluoroaryl)borate compound or tris(fluoroaryl)borate compound as a solid from the aqueous solution. Namely, the solid tetrakis(fluoroaryl)borate compound or tris(fluoroaryl)borate compound containing no impurities can be obtained.

Next, the following description will explain a method for preparing a tetrakis(fluoroaryl)borate derivative by reacting a tetrakis(fluoroaryl)borate compound or tris(fluoroaryl)borate compound obtained by the above purifying method with a compound which forms a monovalent cation seed. More specifically, the present invention will be explained by illustrating, as an example, a method for preparing a tetrakis(fluoroaryl)borate derivative represented by general formula (2) above by reacting a tetrakis(fluoroaryl)borate compound represented by general formula (1) above with a compound which forms a monovalent cation seed.

The compound which forms a monovalent cation seed (hereinafter referred to as the "cation seed generating compound") according to the present invention can be a compound which forms a monovalent cation seed in a later-described reaction solvent and is reactive with a tetrakis(fluoroaryl)borate compound or tris(fluoroaryl)borate compound.

Specific examples of the monovalent cation seed formed by the cation seed generating compound include:

ammonium cations, such as n-butyl ammonium, dimethyl ammonium, trimethyl ammonium, triethyl ammonium, triisopropyl ammonium, tri-n-butyl ammonium, tetramethyl ammonium, tetraethyl ammonium, and tetra-n-butyl ammonium;

anilinium cations, such as anilinium, N-methyl anilinium, N,N-dimethyl anilinium, N,N-diethyl anilinium, N,N-diphenyl anilinium, and N,N,N-trimethyl anilinium;

pyridinium cations, such as pyridinium, N-methyl pyridinium, and N-benzyl pyridinium;

quinolinium cations, such as quinolinium, and isoquinolinium;

adamantyl cations, such as adamantan-2-yl-ammonium;

phosphonium cations, such as dimethylphenyl phosphonium, triphenyl phosphonium, tetraethyl phosphonium, and tetraphenyl phosphonium;

sulfonium cations, such as trimethyl sulfonium, and triphenyl sulfonium;

iodonium cations, such as diphenyl iodonium, and di-4-methoxyphenyl iodonium;

carbenium cations, such as triphenyl carbenium, and tri-4-methoxyphenyl carbenium; and monovalent cations of metals other than alkali metals and alkaline earth metals. However, the monovalent cation seed is not particularly limited to these examples.

Among these compounds, trialkyl ammonium cations, tetraalkyl ammonium cations, dialkyl anilinium cations, alkyl pyridinium cations, tetraalkyl phosphonium cations, tetraaryl phosphonium cations, and diaryl iodonium cations are more preferred. Note that the anionic seed which forms a pair with the monovalent cation seed is not particularly restricted.

Specific examples of the cation seed generating compound include:

quaternary ammonium compounds, such as tri-n-butyl amine.hydrochloride, N,N-dimethylaniline.hydrochloride, N,N-dimethylaniline sulfate, tri-n-butyl ammonium.hydrochloride, and tetramethylammonium chloride;

nitrogen-containing aromatic heterocyclic compounds, such as pyridine hydrochloride, quinoline hydrochloride, N-methylpyridine iodide, and N-methylquinoline iodide;

adamantane compounds, such as 2-aminoadamantane hydrochloride;

quaternary phosphonium compounds, such as tetra-n-butyl phosphonium bromide, and tetraphenyl phosphonium bromide;

sulfonium compounds, such as trimethyl sulfonium chloride, and trimethyl sulfonium iodide;

iodonium compounds, such as diphenyl iodonium chloride; and carbenium compounds, such as tritylchloride (triphenylcarbenium chloride).

For example, N,N-dimethylaniline hydrochloride forms N,N-dimethylanilinium cation as the monovalent cation seed. In this case, the anionic seed is a chlorine ion.

The amount to be used of the compound generating cation seed is not particularly restricted if it is not less than 0.8 equivalent of the tetrakis(fluoroaryl)borate compound or tris(fluoroaryl)borate compound.

In the preparation method of the present invention, a reaction solvent is used. Specific examples of the reaction solvent include: water; solvents of the ether series, such as diethyl ether, dipropyl ether, diisopropyl ether, dibutyl ether, t-butyl methyl ether, diisoamyl ether, 1,2-dimethoxyethane, 1,2-diethoxyethane, anisole, tetrahydrofuran, tetrahydropyran, and 1,4-dioxane; solvents of the aliphatic hydrocarbon series, such as pentane, hexane, and heptane; solvents of the alicyclic hydrocarbons, such as cyclopentane, cyclohexane, and methylcyclohexane; solvents of the ester series, such as methyl acetate, and ethyl acetate; solvents of the aromatic hydrocarbon series, such as benzene, toluene, and xylene; solvents of the alcohol series, such as methyl alcohol and ethyl alcohol; and solvents of the ketone series, such as acetone, and methyl ethyl ketones. However, the reaction solvent is not particularly limited to these examples. It is possible to use only one kind or more than one kind of these compounds.

Moreover, for the reaction using an aqueous solution of a tetrakis(fluoroaryl)borate compound or tris(fluoroaryl) borate compound obtained by the above-mentioned purifying method, water in which the tetrakis(fluoroaryl)borate compound or tris(fluoroaryl)borate compound is dissolved can be used as the reaction solvent (or part of the reaction solvent). Therefore, according to the preparation method of the present invention, it is possible to prepare a tetrakis (fluoroaryl)borate derivative with the use of the solution, without isolating the purified tetrakis(fluoroaryl)borate compound from the aqueous solution of the compound or tris(fluoroaryl)borate compound.

Specific examples of the method of mixing a tetrakis (fluoroaryl)borate compound or tris(fluoroaryl)borate compound and a cation seed generating compound include: a method of mixing a tetrakis(fluoroaryl)borate compound or tris(fluoroaryl)borate compound and a cation seed generating compound in the reaction solvent; a method of mixing a cation seed generating compound or a solution thereof in an aqueous solution of a tetrakis(fluoroaryl)borate compound or tris(fluoroaryl)borate compound; and a method of mixing a tetrakis(fluoroaryl)borate compound or tris(fluoroaryl) borate compound or an aqueous solution thereof in a solution of a cation seed generating compound. However, the method of mixing a tetrakis(fluoroaryl)borate compound or tris(fluoroaryl)borate compound and a cation seed generating compound is not particularly limited to these examples. When mixing the solution of a cation seed generating compound in the aqueous solution of a tetrakis(fluoroaryl) borate compound or tris(fluoroaryl)borate compound or when mixing the aqueous solution of a tetrakis(fluoroaryl) borate compound or tris(fluoroaryl)borate compound in the solution of a cation seed generating compound, it is preferred to introduce the solution to be added, by dropping.

The temperature and time, i.e., the reaction conditions for the reaction of the tetrakis(fluoroaryl)borate compound or tris(fluoroaryl)borate compound with the cation seed generating compound, are not particularly restricted. According to the preparation method of the present invention, by stirring a reaction liquid, which is prepared by dissolving the tetrakis (fluoroaryl)borate compound or tris(fluoroaryl)borate compound and the cation seed generating compound in a reaction solvent, at room temperature for a predetermined time, the reaction can proceed easily. It is therefore possible to easily obtain a tetrakis(fluoroaryl)borate derivative as an object.

For instance, when the tetrakis(fluoroaryl)borate compound is an alkali metal salt of tetrakis(fluoroaryl)borate, an alkaline earth metal salt of tetrakis(fluoroaryl)borate or an alkaline earth metal halide salt of tetrakis(fluoroaryl)borate, and when the cation seed generating compound is N,N-dimethylaniline.hydrochloride, N,N-dimethylanilinium tetrakis(fluoroaryl)borate as an object is obtained by the reaction therebetween, and alkali metal chlorides such as sodium chloride or alkaline earth metal chlorides such as calcium chloride are given as by-products. These alkali metal chlorides or alkaline earth metal chlorides can be easily separated and removed from the solution of N,N-dimethylanilinium·tetrakis (fluoroaryl)borate by, for example, performing separation, filtration, washing, etc.

Moreover, for example, when the tetrakis(fluoroaryl) borate compound is a hydrogen compound of tetrakis (fluoroaryl)borate and when the cation seed generating compound is N,N-dimethylaniline.hydrochloride, N,N-dimethylanilinium tetrakis (fluoroaryl) borate as an object is obtained by the reaction therebetween, and a hydrochloric acid is given as a by-product. The hydrochloric acid can be easily separated and removed from N,N-dimethylanilinium·tetrakis (fluoroaryl)borate by, for example, performing separation, washing, etc.

In other words, the tetrakis(fluoroaryl)borate derivative can be easily isolated and purified as a crystal by performing a simple process, for example, the removal of the reaction solvent (by distillation), if necessary, after performing a simple process such as separation and filtration.

As described above, the method for preparing a tetrakis (fluoroaryl)borate derivative according to the present invention is a method of reacting a tetrakis(fluoroaryl)borate compound or tris(fluoroaryl)borate compound obtained by the above-mentioned purifying method with a cation seed generating compound.

According to this method, it is possible to prepare tetrakis(fluoroaryl)borate derivatives from tetrakis(fluoroaryl)borate compounds, i.e., alkali metal salts of tetrakis(fluoroaryl)borate, alkaline earth metal salts of tetrakis(fluoroaryl)borate, alkaline earth metal halide salts of tetrakis(fluoroaryl)borate and hydrogen compounds of tetrakis(fluoroaryl)borate, efficiently and at low costs. Since the derivatives do not contain colored components and impurities, for example, halogenated magnesium, they have a high purity and can be suitably used as, for example, a co-catalyst of a metallocene catalyst for a cationic complex polymerization reaction and a catalyst for photopolymerization of silicone.

EXAMPLES

The following description will explain in great detail the present invention by illustrating examples. However, the present invention is not limited by these examples.

Example 1

400 ml of a xylene (organic solvent) solution containing 108.8 g (0.160 moles) of a tetrakis(pentafluorophenyl)borate·hydrogen as a crude tetrakis(fluoroaryl)borate compound, and 500 ml of ion-exchange water were placed in a 1-liter reaction vessel equipped with a thermometer, a stirrer and a reflux condenser. The purity of the tetrakis(pentafluorophenyl)borate·hydrogen in the solution was 95.4%. Moreover, the solution was colored black by colored components.

Next, the mixture was heated and stirred at 100° C. for 4 hours. Subsequently, the stirring was stopped, and the mixture was cooled to 70° C. As a result, the mixture separated into two layers, i.e., a black xylene layer and a colorless transparent aqueous layer. Then, by performing separation (oil and water separation), only the aqueous layer was separated.

The content of the tetrakis(pentafluorophenyl)borate·hydrogen in the aqueous layer was found by measuring $^{19}$F-NMR (nuclear magnetic resonance) spectrum. More specifically, by using p-fluorotoluene as an internal standard, $^{19}$F-NMR was measured under predetermined conditions. In the measurement, a trifluoroacetic acid was used as a standard material, and the position of the signal was made 0 ppm. Then, the integrated value of fluorine atoms of p-fluorotoluene and the integrated value of fluorine atoms in the ortho position of the pentafluorophenyl group of the tetrakis(pentafluorophenyl)borate·hydrogen were obtained from the chart of the $^{19}$F-NMR, and the amount of the tetrakis(pentafluorophenyl) borate·hydrogen was calculated from the integrated values. As a result, it was found that 79.4 g of colorless tetrakis(pentafluorophenyl) borate·hydrogen was contained in the aqueous layer, and the purity was 99.0%. Besides, the recovery of the tetrakis(pentafluorophenyl)borate hydrogen was 73.0%.

Example 2

A solution containing 108.8 g (0.160 moles) of a crude (purity: 95.4%) tetrakis(pentafluorophenyl) borate·hydrogen and 320 ml of xylene, and 400 ml of ion-exchange water were placed in a 1-liter reaction vessel equipped with a thermometer, a dropping funnel, a stirrer and a distillation apparatus. The solution was colored black by colored components.

Next, the mixture was heated to 100° C. with stirring in order to remove xylene by distillation. Water which distilled off by forming an azeotropic composition with xylene was separated, and then returned to the reaction vessel through the dropping funnel. The heating was stopped at the time 200 ml of xylene was removed by distillation, and the mixture was cooled to 70° C. As a result, the mixture separated into two layers, i.e., a black xylene layer and a white aqueous layer. Then, by performing separation, only the aqueous layer was separated.

It was found as a result of performing the analysis in the same manner as in Example 1 that 98.1 g of colorless tetrakis(pentafluorophenyl)borate hydrogen was contained in the aqueous layer, and the purity was 99.0%. Further, the recovery of the tetrakis(pentafluorophenyl)borate·hydrogen was 90.2%.

Example 3

400 ml of a xylene solution containing 108.8 g (0.160 moles) of a crude (purity: 95.4%) tetrakis(pentafluorophenyl)borate hydrogen, and 600 ml of ion-exchange water were placed in the same reaction vessel as in Example 2. The solution was colored black by colored components.

Next, the mixture was heated to 100° C. with stirring in order to remove xylene by distillation. Water which distilled off by forming an azeotropic composition with xylene was separated, and then returned to the reaction vessel through the dropping funnel. The heating was stopped at the time the removal of xylene by distillation was completed, and the mixture was cooled to 70° C. As a result, the mixture separated into two layers, i.e., a white aqueous layer and a black oily layer remaining at the bottom of the reaction vessel, and only the aqueous layer was separated.

It was found as a result of performing the analysis in the same manner as in Example 1 that 105.5 g of colorless tetrakis(pentafluorophenyl) borate·hydrogen was contained in the aqueous layer, and the purity was 99.0%. Further, the recovery of the tetrakis(pentafluorophenyl)borate·hydrogen was 97.0%.

Example 4

400 ml of a di-n-butyl ether solution containing 108.8 g (0.160 moles) of a crude (purity: 95.5%) tetrakis(pentafluorophenyl)borate·hydrogen, and 500 ml of ion-exchange water were placed in the same reaction vessel as in Example 2. The solution was colored black by colored components.

Next, the mixture was heated to 100° C. with stirring in order to remove di-n-butyl ether by distillation. Moreover, water which distilled off by forming an azeotropic composition with di-n-butyl ether was separated, and then returned to the reaction vessel through the dropping funnel. The heating was stopped at the time the removal of di-n-butyl ether by distillation was completed, and the mixture was cooled to 70° C. As a result, a black oily layer remained at the bottom of the reaction vessel.

Thereafter, 100 ml of toluene as an aromatic hydrocarbon was placed in the reaction vessel through the dropping funnel, and heated and stirred at 70° C. for one hour. When the stirring was stopped, the mixture was separated into two layers, i.e., a black toluene layer and a colorless transparent aqueous layer. Then, by performing separation, only the aqueous layer was extracted from the reaction vessel.

It was found as a result of performing the analysis in the same manner as in Example 1 that 103.4 g of colorless tetrakis(pentafluorophenyl) borate·hydrogen was contained in the aqueous layer, and the purity was 99.06. Further, the recovery of the tetrakis(pentafluorophenyl)borate hydrogen was 95.0%.

Example 5

230 ml of ion-exchange water was placed in a 1-liter container equipped with a thermometer, a stirrer and a Soxhlet extractor for heavy specific gravity. Moreover, 65 ml of a xylene solution containing 16.3 g (0.024 moles) of a crude (purity: 95.06) tetrakis(pentafluorophenyl) borate·hydrogen, and 400 ml of ion-exchange water were placed in the Soxhlet extractor. The solution was colored black by colored components.

Next, after carrying out reflux intermittently for 60 hours while stirring the ion-exchange water in the reaction vessel to perform extraction, heating and stirring were stopped. The aqueous solution (extract) in the reaction vessel and the aqueous layer in the Soxhlet extractor were colorless and transparent. The aqueous layer in the Soxhlet extractor was separated and this aqueous solution and extract were combined.

It was found as a result of performing the analysis in the same manner as in Example 1 that 11.0 g of colorless tetrakis(pentafluorophenyl)borate·hydrogen was contained in the mixture, and the purity was 99.0%. Further, the recovery of the tetrakis(pentafluorophenyl)borate hydrogen was 64.7%.

Example 6

400 ml of a di-n-butyl ether solution containing 112.3 g (0.160 moles) of sodium tetrakis(pentafluorophenyl) borate as a crude (purity: 95.5%) tetrakis(fluoroaryl)borate compound, and 600 ml of ion-exchange water were placed in the same reaction vessel as in Example 2. The solution was colored black by colored components.

Next, the mixture was heated to 100° C. with stirring in order to remove di-n-butyl ether by distillation. Moreover, water which distilled off by forming an azeotropic composition with di-n-butyl ether was separated, and then returned to the reaction vessel through the dropping funnel. The heating was stopped at the time the removal of di-n-butyl ether by distillation was completed, and the mixture was cooled to 70° C. As a result, a black oily layer remained at the bottom of the reaction vessel.

Thereafter, 200 ml of toluene was placed in the reaction vessel through the dropping funnel, and heated and stirred at 70° C. for one hour. Subsequently, the mixture was cooled to 50° C. When the stirring was stopped, the mixture separated into two layers, i.e., a black toluene layer and an aqueous layer. Then, by performing separation, only the aqueous layer was extracted from the reaction vessel.

It was found as a result of performing the analysis in the same manner as in Example 1 that 104.6 g of colorless sodium tetrakis(pentafluorophenyl)borate was contained in the aqueous layer, and the purity was 99.0%. Further, the recovery of the sodium tetrakis(pentafluorophenyl)borate was 93.1%.

Example 7

80 ml of a xylene solutionl containing 103.4 g (0.132 moles) of tetrakis(pentafluorophenyl) boratedmagnesium bromide as a crude (purity: 95.5%) tetrakis (fluoroaryl) borate compound, and 125 ml of ion-exchange water were placed in the same reaction vessel as in Ex ampl e 2. The solution was colored black by colored comp onents.

Next, the mixtu re was heated to 100° C. with stirring in order to remove xylene by distillation. The heating was stopped at the time the removal of xylene by distillation was completed, and the mixture was cooled to 70° C. As a result, the mixture was separated into two layers, i.e., a white aqueous layer and a black oily layer remaining at the bottom of the container, and only the aqueous layer was extracted from the reaction vessel.

It was found as a result of performing the analysis in the same manner as in Example 1 that 55.0 g of colorless tetrakis(pentafluorophenyl) borate·magnesium bromide was contained in the aqueous layer, and the purity was 99.0%. Further, the recovery of the tetrakis (pentafluorophenyl) borate·magnesium bromide was 61.3%.

Example 8

An aqueous solution containing 79.4 g (0.117 moles) of the tetrakis(pentafluorophenyl )borate·hydrogen which was purified in Example 1 was placed in a 1-liter reaction vessel equipped with a thermometer, a dropping funnel, a stirrer and a reflux condenser. Meanwhile, 130 ml of an aqueous solution containing 0.155 moles of N,N-dimethylaniline·sulfate as a cation seed generating compound was charged to the dropping funnel.

Next, the aqueous solution in the reaction vessel was heated to 70° C. while stirring the aqueous solution. Thereafter, the aqueous solution in the dropping funnel was dropped at the same temperature over 30 minutes. After the dropping was completed, the reaction solution was cooled to room temperature. Whereby the reaction solution was crystallized. Then, the crystal was collected by suction filtration. The resultant cake (crystal) was washed with 160 ml of ion-exchange water, and then dried under reduced pressure.

Consequently, N,N-dimethylanilinium·tetrakis (pentafluorophenyl)borate as a tetrakis(fluoroaryl)borate derivative was obtained as white powder. It was found as a result of performing the analysis in the same manner as in Example 1 that the yield of N,N-dimethylanilinium.tetrakis (pentafluorophenyl)borate was 95.0 mole % based on the tetrakis(pentafluorophenyl)borate hydrogen, and the purity was 99.0%.

Example 9

An aqueous solution containing 105.5 g (0.155 moles) of the tetrakis(pentafluorophenyl) borate·hydrogen which was purified in Example 3 was charged to the same reaction vessel as in Example 8. Meanwhile, 130 ml of an aqueous solution containing 0.155 moles of N,N-dimethylaniline·sulfate was charged to the dropping funnel.

Next, by performing the same reaction and operation as in Example 8, N,N-dimethylanilinium·tetrakis (pentafluorophenyl)borate was obtained as white powder. It was found as a result of performing the analysis in the same manner as in Example 1 that the yield of N,N-dimethylanilinium·tetrakis (pentafluorophenyl)borate was 90.0 mole based on the tetrakis(pentafluorophenyl) borate.hydrogen, and the purity was 99.0%.

Example 10

An aqueous solution containing 103.4 g (0.152 moles) of the tetrakis(pentafluorophenyl) borate·hydrogen which was purified in Example 4 was charged to the same reaction vessel as in Example 8. Meanwhile, 130 ml of an aqueous solution containing 0.155 moles of N,N-dimethylaniline.sulfate was charged to the dropping funnel.

Next, by performing the same reaction and operation as in Example 8, N,N-dimethylanilinium.tetrakis (pentafluorophenyl) borate was obtained as white powder. It was found as a result of performing the analysis in the same manner as in Example 1 that the yield of N,N-dimethylanilinium·tetrakis (pentafluorophenyl)borate was 95.0 mole based on the tetrakis(pentafluorophenyl) borate.hydrogen, and the purity was 99.0%.

Example 11

An aqueous solution containing 10.5 g (0.015 moles) of the sodium tetrakis(pentafluorophenyl)borate purified in Example 6 was charged to the same reaction vessel as in Example 8. Meanwhile, 13 ml of an aqueous solution containing 0.015 moles of N,N-dimethylaniline.sulfate was charged to the dropping funnel.

Next, by performing the same reaction and operation as in Example 8 except that the amount of the ion-exchange water for washing the cake was changed to 60 ml, N,N-dimethylanilinium·tetrakis (pentafluorophenyl)borate was obtained as white powder. It was found as a result of performing the analysis in the same manner as in Example 1 that the yield of N,N-dimethylanilinium tetrakis (pentafluorophenyl) borate was 95.0 mole % based on the sodium tetrakis(pentafluorophenyl)borate, and the purity was 99.0%.

Example 12

The same reaction and operation as in Example 11 were performed except that 20 ml of an aqueous solution containing 0.018 moles of tetramethylammonium.hydrochloride as a cation seed generating compound was used instead of the aqueous solution of N,N-dimethylaniline sulfate.

As a result, tetramethylammonium tetrakis (pentafluorophenyl) borate as a tetrakis(fluoroaryl)borate derivative was obtained as white powder. It was found as a result of performing the analysis in the same manner as in Example 1 that the yield of the tetramethylammonium.tetrakis (pentafluorophenyl) borate was 97.4 mole % based on the sodium tetrakis(pentafluorophenyl)borate, and the purity was 99.0%.

Example 13

The same reaction and operation as in Example 11 were performed except that 20 ml of an aqueous solution containing 0.015 moles of tri-n-butylammonium-hydrochloride as a cation seed generating compound was used instead of the aqueous solution of N,N-dimethylaniline·sulfate.

As a result, tri-n-butylammonium·tetrakis (pentafluorophenyl)borate as a tetrakis(fluoroaryl)borate derivative was obtained as white powder. It was found as a result of performing the analysis in the same manner as in Example 1 that the yield of the tri-n-butylammonium·tetrakis(pentafluorophenyl)borate was 96.5 mole % based on the sodium tetrakis(pentafluorophenyl) borate, and the purity was 99.0%.

Example 14

The same reaction and operation as in Example 11 were performed except that 20 ml of an aqueous solution containing 0.015 moles of tetra-n-butylphosphonium bromide as a cation seed generating compound was used instead of the aqueous solution of N,N-dimethylaniline sulfate.

As a result, tetra-n-butylphosphonium.tetrakis (pentafluorophenyl)borate as a tetrakis(fluoroaryl)borate derivative was obtained as white powder. It was found as a result of performing the analysis in the same manner as in Example 1 that the yield of the tetra-n-butylphosphonium.tetrakis(pentafluorophenyl)borate was 83.9 mole % based on the sodium tetrakis (pentafluorophenyl)borate, and the purity was 99.0%.

Example 15

The same reaction and operation as in Example 11 were performed except that 20 ml of an aqueous solution containing 0.016 moles of trimethylsulfonium iodide as a cation seed generating compound was used instead of the aqueous solution of N,N-dimethylaniline·sulfate.

As a result, trimethylsulfonium. tetrakis (pentafluorophenyl)borate as a tetrakis(fluoroaryl)borate derivative was obtained as white powder. It was found as a result of performing the analysis in the same manner as in Example 1 that the yield of the trimethylsulfonium.tetrakis (pentafluorophenyl)borate was 89.5 mole % based on the sodium tetrakis(pentafluorophenyl)borate, and the purity was 99.0%.

Example 16

The same reaction and operation as in Example 11 were performed except that 20 ml of an aqueous solution containing 0.015 moles of pyridine-hydrochloride as a cation seed generating compound was used instead of the aqueous solution of N,N-dimethylaniline·sulfate.

As a result, pyridinium.tetrakis(pentafluorophenyl)borate as a tetrakis(fluoroaryl)borate derivative was obtained as white powder. It was found as a result of performing the analysis in the same manner as in Example 1 that the yield of the pyridinium.tetrakis(pentafluorophenyl)borate was 89.2 mole % based on the sodium tetrakis (pentafluorophenyl)borate, and the purity was 99.0%.

Example 17

The same reaction and operation as in Example 11 were performed except that an aqueous solution containing 8.2 g (0.012 moles) of tetrakis (pentafluorophenyl) borate.sodium was charged to the reaction vessel and 20 ml of an aqueous solution containing 0.012 moles of N-methylquinoline iodide as a cation seed generating compound was used instead of the aqueous solution of N,N-dimethylaniline·sulfate.

As a result, N-methyl quinolinium.tetrakis (pentafluorophenyl)borate as a tetrakis (fluoroaryl)borate derivative was obtained as white powder. It was found as a result of performing the analysis in the same manner as in Example 1 that the yield of the N-methyl quinolinium tetrakis(pentafluorophenyl)borate was 93.5 mole % based on the sodium tetrakis(pentafluorophenyl)borate, and the purity was 99.0%.

Example 18

By distilling water under reduced pressure from an aqueous solution containing 14.04 g (0.020 moles) of the sodium tetrakis(pentafluorophenyl)borate which was purified in Example 6, 13.18 g (0.019 moles) of the sodium tetrakis (pentafluorophenyl)borate was obtained as a white solid. The purity of the resultant sodium tetrakis (pentafluorophenyl)borate was 99%, and the recovery thereof from the aqueous solution was 93.9%.

Next, the sodium tetrakis(pentafluorophenyl) borate, 0.019 moles of triphenylcarbenium chloride as a cation seed generating compound and 200 ml of n-hexane (reaction solvent) were charged to a reaction vessel equipped with a thermometer, a stirrer and a reflux condenser. Subsequently, the content was heated while stirring the content to carry out a reaction for 6 hours under reflux.

After the reaction was completed, the reaction mixture was cooled to room temperature. Whereby a yellow crystal was deposited from the reaction solution. Then, the crystal was collected by suction filtration. The resultant cake (crystal) was dissolved in 100 ml of dichloromethane, and insolubles were removed by filtration through Celite. The resultant filtrate was condensed and dried to obtain a solid. Thereafter, the solid was suspended in 100 ml of n-hexane, and stirred for 16 hours. Thereafter, the stirring was stopped, and the precipitate was collected under reduced pressure. Next, the resultant cake was washed with 100 ml of n-hexane, and dried under reduced pressure.

Consequently, triphenylcarbenium·tetrakis (pentafluorophenyl)borate as a tetrakis(fluoroaryl)borate derivative was obtained as yellow powder. It was found as a result of performing the analysis in the same manner as in Example 1 that the yield of triphenylcarbenium.tetrakis (pentafluorophenyl)borate was 30.2 mole % based on the sodium tetrakis(pentafluorophenyl)borate, and the purity was 99.0%.

Example 19

110.10 g of an aqueous solution containing 10.10 g (0.01439 moles) of the sodium tetrakis(pentafluorophenyl) borate which was purified in Example 6, and 30 ml of dichloromethane (organic extracting solvent) were charged to a separating funnel, shaken strongly, and then left to rest. After separating a dichloromethane layer, another 30 ml of dichloromethane was charged to the separating funnel and carried out the same procedure as above. The separating dichloromethane layers were combined and dried over anhydrous sodium sulfate, and concentrated under reduced pressure. As a result, a white solid was obtained. It was found by performing the analysis in the same manner as in Example 1 that the solid contained 9.78 g (0.01393 moles) of sodium tetrakis(pentafluorophenyl)borate, and the purity was 99.0%. Besides, the recovery of sodium tetrakis (pentafluorophenyl)borate was 96.8%.

Next, the sodium tetrakis(pentafluorophenyl)borate, 2.61 g (0.0139 moles) of 2-aminoadamantane.hydrochloride as a cation seed generating compound, and 100 ml of cyclohexane (reaction solvent) were charged to a reaction vessel equipped with a thermometer, a stirrer and a reflux condenser. Subsequently, the reaction mixture was stirred at room temperature (26° C.) for 1 hour and refluxed for 3 hours.

After the completion of the reaction, the reaction mixture was cooled to room temperature. Whereby the reaction solution was crystallized. Then, the crystal was collected by suction filtration. The resultant cake (crystal) was washed with 100 ml of ion-exchange water, and then dried at 70° C. for 12 hours under reduced pressure.

As a result, adamantan-2-yl-ammonium.tetrakis (pentafluorophenyl)borate as a tetrakis (fluoroaryl)borate derivative was obtained as a white crystal. It was found as a result of performing the analysis in the same manner as in Example 1 that the yield of adamantan-2-yl-ammonium.tetrakis(pentafluorophenyl)borate was 88.2 mole % based on the sodium tetrakis(pentafluorophenyl) borate, and the purity was 99.0%.

Example 20

30 ml of a di-n-butyl ether solution containing 12.3 g (0.0216 moles) of a crude (purity: 86.5%) n-butyl-tris (pentafluorophenyl)borate hydrogen, and 150 ml of ion-exchange water were charged to the same reaction vessel as in Example 2. The solution was colored black by the colored components.

Next, di-n-butyl ether was removed by distillation by heating the mixture to 100° C. while stirring the mixture. Moreover, water which distilled off by the formation of an azeotropic composition with di-n-butyl ether was separated, and then returned to the reaction vessel through the dropping funnel. The heating was stopped at the time the distillation of di-n-butyl ether was completed, and the mixture was cooled to 70° C. As a result, the mixture separated into two layers, i.e., a white aqueous layer and a black oily layer remaining at the bottom of the reaction vessel. Then, only the aqueous solution was separated. Thus, the n-butyl-tris (pentafluorophenyl)borate·hydrogen was purified.

Subsequently, the aqueous solution containing the n-butyl-tris(pentafluorophenyl)borate·hydrogen purified in the above-described method was charged to the same reaction vessel as that used in Example 8. Meanwhile, 50 ml of an aqueous solution containing 0.025 moles of tetramethylammonium chloride was charged to the dropping funnel.

Next, by performing the same reaction and operation as in Example 8, 10.30 g of tetramethylammonium.n-butyl-tris (pentafluorophenyl) borate was obtained as white powder. It was found as a result of performing the analysis in the same manner as in Example 1 that the yield of tetramethylammonium.n-butyl-tris(pentafluorophenyl) borate was 75.0 mole % based on the n-butyl-tris (pentafluorophenyl) borate·hydrogen, and the purity was 96.0%.

Example 21

30 ml of a di-n-butyl ether solution containing 1.54 g (0.0025 moles) of crude (purity: 90.0%) sodium cyclohexyl-tris(pentafluorophenyl)borate, and 50 ml of ion-exchange water were charged to the same reaction vessel as in Example 2. The solution was colored black by the colored components.

Next, di-n-butyl ether was removed by distillation by heating the mixture to 100° C. while stirring the mixture. Moreover, water which distilled off by the formation of an azeotropic composition with di-n-butyl ether was separated, and then returned to the reaction vessel through the dropping funnel. The heating was stopped at the time the distillation of di-n-butyl ether was completed, and the mixture was cooled to 70° C. As a result, the mixture separated into two layers, i.e., a white aqueous layer and a black oily layer remaining at the bottom of the reaction vessel. Then, only the aqueous solution was separated. Thus, cyclohexyl-tris (pentafluorophenyl) borate-sodium was purified.

Subsequently, the aqueous solution containing the sodium cyclohexyl-tris(pentafluorophenyl)borate purified in the above-described method was charged to the same reaction vessel as that used in Example 8. Meanwhile, 30 ml of an aqueous solution containing 0.005 moles of tetramethylammonium chloride was charged to the dropping funnel.

Next, by performing the same reaction and operation as in Example 8, 1.54 g of tetramethylammonium-cyclohexyl-tris (pentafluorophenyl)borate was obtained as white powder. It was found as a result of performing the analysis in the same manner as in Example 1 that the yield of tetramethylammonium cyclohexyl-tris(pentafluorophenyl)borate was 92.0 mole % based on the sodium cyclohexyl-tris (pentafluorophenyl)borate, and the purity was 99.0%.

The invention being thus described, it will be obvious that the same may be varied in many ways. Such variations are not to be regarded as a departure from the spirit and scope of the invention, and all such modifications as would be obyious to one skilled in the art are intended to be included within the scope of the following claims.

What is claimed is:

1. A method for purifying a tetrakis(fluoroaryl)borate compound or a tris(fluoroaryl)borate compound, characterized by mixing a solution containing an organic solvent and the tetrakis(fluoroaryl)borate compound or the tris(fluoroaryl)borate compound including impurities, with water, and wherein, after mixing the solution with water, an aqueous solution obtained by removing the organic solvent from the mixture by distillation is further mixed with an aromatic hydrocarbon.

2. The method for purifying a tetrakis(fluoroaryl)borate compound or a tris(fluoroaryl)borate compound as set forth in claim 1, wherein the tetrakis(fluoroaryl)borate compound or the tris(fluoroaryl)borate compound is a compound represented by formula (3)

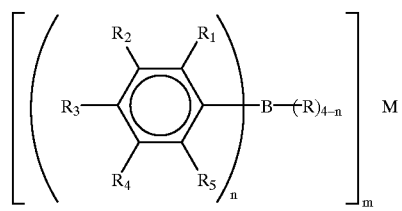

(3)

wherein R is an alkyl group having 1 to 20 carbon atoms or a cycloalkyl group having 3 to 10 carbon atoms or a cycloalkyl group having 3 to 10 carbon atoms, $R_1$, $R_2$, $R_3$, $R_4$ and $R_5$ independently represent a hydrogen atom, a fluorine atom, a hydrocarbon group or an alkoxy group, at least one of $R_1$ to $R_5$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal.

3. The method for purifying a tetrakis(fluoroaryl)borate compound or a tris(fluoroaryl)borate compound as set forth in claim 1, wherein the tetrakis(fluoroaryl)borate compound or the tris(fluoroaryl)borate compound is a compound represented by formula (1)

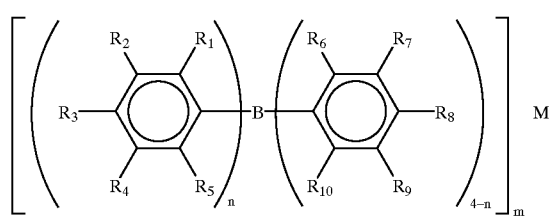

(1)

wherein $R_1$, $R_2$, $R_5$, $R_6$, $R_7$, $R_8$, $R_9$ and $R_{10}$ independently represent a hydrogen atom, a fluorine atom, a hydrocarbon group or an alkoxy group, at least one of $R_6$ to $R_{10}$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal.

4. The method for purifying a tetrakis(fluoroaryl)borate compound or a tris(fluoroaryl)borate compound as set forth in claim 1, wherein the organic solvent is removed by distillation so that the organic solvent is not more than 30% by weight based on a weight of water.

5. The method for purifying a tetrakis(fluoroaryl)borate compound or a tris(fluoroaryl)borate compound as set forth in claim 1, wherein the organic solvent is removed by distillation so that the organic solvent is not more than 30% by weight based on a weight of water.

6. The method for purifying a tetrakis(fluoroaryl)borate compound or a tris(fluoroaryl)borate compound as set forth in claim 1, wherein the tetrakis(fluoroaryl)borate compound or a tris(fluoroaryl)borate compound is isolated as a solid from an aqueous solution of tetrakis (fluoroaryl) borate compound or a tris(fluoroaryl)borate compound obtained by mixing said solution with water.

7. The method for purifying a tetrakis(fluoroaryl)borate compound or a tris(fluoroaryl)borate compound as set forth in claim 6, wherein water is removed from the aqueous solution by distillation.

8. The method for purifying a tetrakis(fluoroaryl)borate compound or a tris(fluoroaryl)borate compound as set forth in claim 6, wherein the aqueous solution is condensed and/or cooled to separate the tetrakis(fluoroaryl)borate compound or a tris(fluoroaryl)borate compound.

9. The method for purifying a tetrakis(fluoroaryl)borate compound or a tris(fluoroaryl)borate compound as set forth in claim 6, wherein the aqueous solution is mixed with an organic extraction medium which dissolves the tetrakis (fluoroaryl)borate compound or a tris(fluoroaryl)borate compound and is not evenly mixed with water.

10. A method for preparing a tetrakis(fluoroaryl)borate derivative, characterized by reacting a compound generating a monovalent cation seed with a tetrakis(fluoroaryl)borate compound or a tris(fluoroaryl)borate compound, wherein the tetrakis(fluoroaryl)borate compound or the tris(fluoroaryl) borate compound has been purified prior to reaction with the comoound generating a monovalent cation seed by mixing a solution containing an organic solvent and the tetrakis (fluoroaryl)borate compound or the tris(fluoroaryl)borate compound including impurities with water followed by removing the organic solvent from the mixture by distillation.

11. The method for preparing a tetrakis(fluoroaryl)borate derivative as set forth in claim 10, wherein the tetrakis (fluoroaryl)borate compound or the tris(fluoroaryl)borate compound is a compound represented by formula (3)

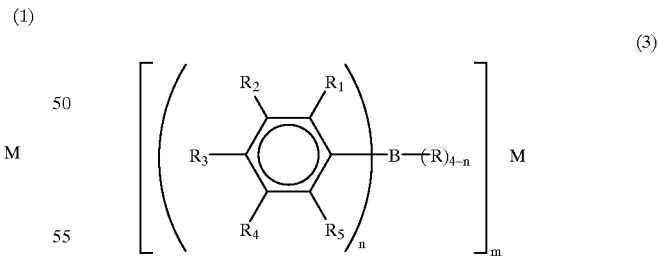

(3)

wherein R is an alkyl group having 1 to 20 carbon atoms or a cycloalkyl group having 3 to 10 carbon atoms or a cycloalkyl group having 3 to 10 carbon atoms, $R_1$, $R_2$, $R_3$, $R_4$ and $R_5$ independently represent a hydrogen atom, a fluorine atom, a hydrocarbon group or an alkoxy group, at least one of $R_1$ to $R_5$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal.

12. The method for preparing a tetrakis(fluoroaryl)borate derivative as set forth in claim 10, wherein the tetrakis(fluoroaryl)borate compound or a tris(fluoroaryl)borate compound is a compound represented by formula (1)

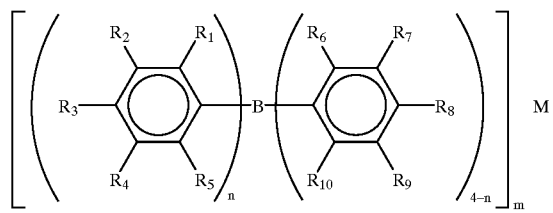

(1)

(wherein $R_1$, $R_2$, $R_3$, $R_4$, $R_5$, $R_6$, $R_7$, $R_8$, $R_9$ and $R_{10}$ independently represent a hydrogen atom, a fluorine atom, a hydrocarbon group or an alkoxy group, at least one of $R_1$ to $R_5$ is a fluorine atom, at least one of $R_6$ to $R_{10}$ is a fluorine atom, M is a hydrogen atom, alkali metal, alkaline earth metal or alkaline earth metal halide, n is 3 or 4, and m is 1 when M is a hydrogen atom, alkali metal or alkaline earth metal halide, or m is 2 when M is an alkaline earth metal.

13. The method for preparing a tetrakis(fluoroaryl)borate derivative as set forth in claim 12, wherein the tetrakis(fluoroaryl)borate derivative is a compound represented by formula (2)

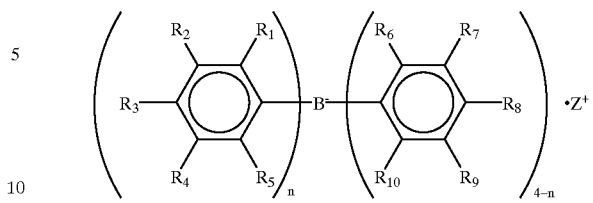

(2)

(wherein $R_1$, $R_2$, $R_3$, $R_4$, $R_5$, $R_6$, $R_7$, $R_8$, $R_9$ and $R_{10}$ independently represent a hydrogen atom, a fluorine atom, a hydrocarbon group or an alkoxy group, at least one of $R_1$ to $R_5$ is a fluorine atom, at least one of $R_6$ to $R_{10}$ is a fluorine atom, $Z^+$ is a monovalent cation seed, and n is 3 or 4.

14. A method for preparing a tetrakis(fluoroaryl)borate derivative, characterized by purifying a tetrakis(fluoroaiyl)borate compound or a tris(fluoroaryl)borate compound by rnmxing a solution containing an organic solvent and the tetralis(fluoroaryl)borate compound or the tris(fluoroaryl)borate compound including impurities with water then removing the organic solvent from the mixture by distillation, followed by reacting a compound generating a monovalent cation seed with the purified tetraikis(fluoroaryl)borate compound or the tris(fluoroaryl)borate compound.

* * * * *